US006471719B1

(12) United States Patent
Voinov et al.

(10) Patent No.: US 6,471,719 B1
(45) Date of Patent: Oct. 29, 2002

(54) DOUBLE-SHEET STENT

(76) Inventors: Valerian Voinov, 52/58 Bar-Yohai St., Jerusalem 93345 (IL); Romul Boldyrev, 9 Brand St. #3, Jerusalem (IL), 93878

( * ) Notice: Subject to any disclaimer, the term of this patent is extended or adjusted under 35 U.S.C. 154(b) by 104 days.

(21) Appl. No.: 09/705,385

(22) Filed: Nov. 3, 2000

Related U.S. Application Data

(63) Continuation of application No. PCT/IL99/00221, filed on Apr. 25, 1999.
(51) Int. Cl.[7] .................................................. A61F 2/06
(52) U.S. Cl. ...................................... 623/1.12; 623/901
(58) Field of Search ............................... 623/1.15, 1.16, 623/901; 29/505

(56) References Cited

U.S. PATENT DOCUMENTS

| | | | |
|---|---|---|---|
| 5,813,975 A | | 9/1998 | Valenti |
| 5,824,052 A | | 10/1998 | Khosravi et al. |
| 5,907,893 A | | 6/1999 | Zadno-Azizi et al. |
| 5,916,264 A | | 6/1999 | Von Oepen et al. |
| 6,245,102 B1 | * | 6/2001 | Jayarman .................... 623/1.15 |
| 6,316,096 B1 | * | 11/2001 | Yoshida et al. .............. 428/331 |
| 6,327,772 B1 | * | 12/2001 | Zadno-Azizi et al. ......... 29/557 |

FOREIGN PATENT DOCUMENTS

EP       WO 00/64372     * 11/2000     ................. 623/1.15

* cited by examiner

*Primary Examiner*—Corrine McDermott
*Assistant Examiner*—Suzette J. Jackson

(74) *Attorney, Agent, or Firm*—Reed Smith LLP

(57) ABSTRACT

A double-sheet stent for insertion into a lumen of a vessel of living being, comprises constructive elements, preliminary formed in a shape of the two mainly similar stencils I and II on the surface of the two thin sheet metallic blanks. The stencils I and II are preliminary superimposed one on another in order to be shifted for a winding outline width along the stent longitudinal axis and to form the alternating winding outlines pairs. One pair of the winding outlines is executed by a simple superimposing of the stencil I winding outline (12) on the stencil II winding outline (14), whereas the winding outlines pair, neighboring to it, is performed by the superimposing of the stencil II winding outline (15) on the stencil I winding outline (13). The stencil II winding outlines are passed through the slots between the stencil I winding outlines as to make the formed semicircles be located in turns in the stent expanded shape. One semicircle belongs to stencil I, while the neighboring one belongs to stencil II, and this sequence of the semicircles location is preserved also on the opposite side in relation to the relatively rigid bands along the stent longitudinal axis and II are connected into one surface along the common longitudinal axis of the sheet blank symmetry by one relatively rigid band in such a way that the stencil I winding outlines are the continuation of the stencil II winding outlines, but the winding outlines of the thin sheet blank edges are connected along the longitudinal axis by the two relatively rigid bands, thus forming a double-sheet stencil, the double-sheet stencil is folded, joining the last relatively rigid bands and forming an unsplit joint, whereas in a stent expanded shape all the stencil I formed semicircles are located on one side from the location surface of the relatively rigid bands and all the stencil II formed semicircles are located oppositively on the other side from the location surface of the said relatively rigid bands.

48 Claims, 7 Drawing Sheets

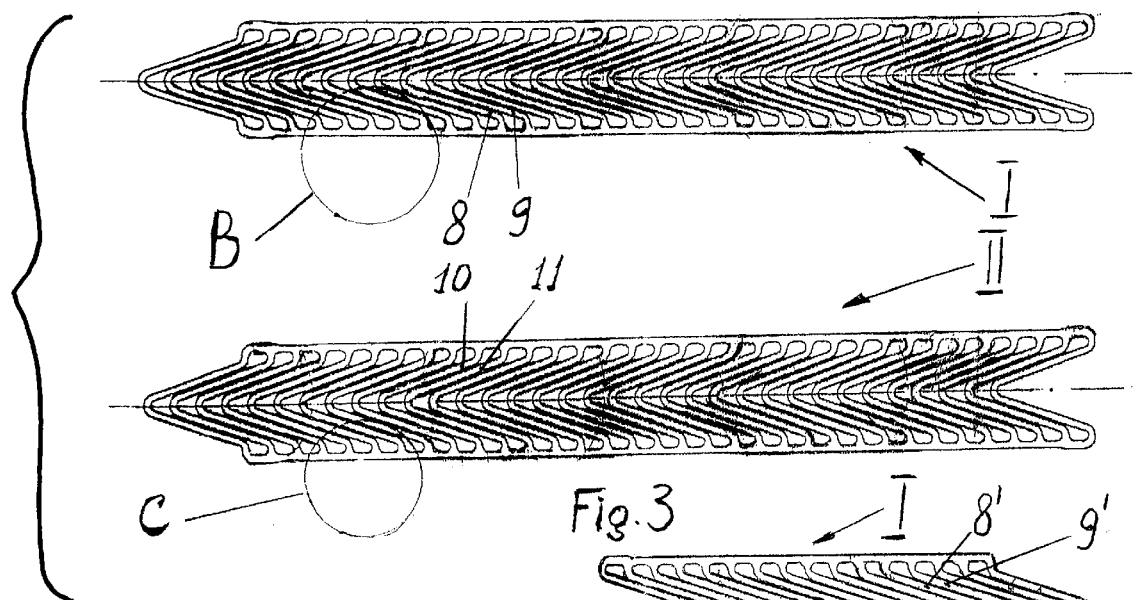
Fig. 3
Fig. 3a
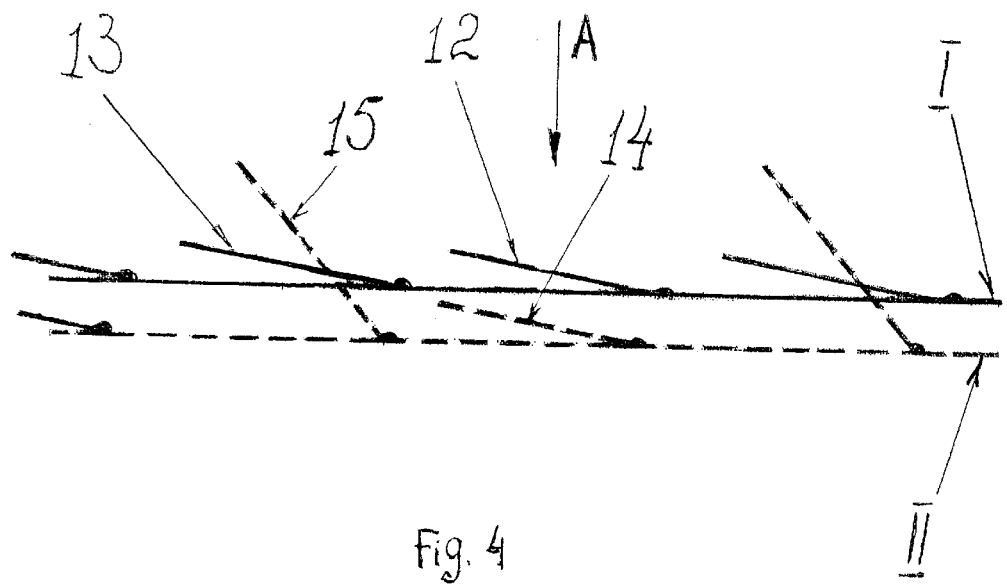
Fig. 4

DOUBLE-SHEET STENT

CROSS-REFERENCE TO RELATED APPLICATION

This patent application is a continuation of co-pending PCT application No. PCT/IL99/0021, filed Apr. 25, 1999.

FIELD OF THE INVENTION

The present invention relates generally to medical technology. The present invention particularly relates to expandable cardiovascular stents which are intended for radial arterial lumen recovery with subsequent restoration of normal blood flow.

BACKGROUND OF THE INVENTION

One of the most perspective tendencies in the development of stents is the design with improved antithrombotic properties to lessen the necessity of systematic anticoagulation therapy and to reduce bleeding and vascular complications. However, all the currently available stents are executed from metal, and in each model there is a compromise between the constructive elements of radial strength and flexibility, to safely support the deformed walls of the artery and, with the least resistance, to prevent the normal pulsation of the vessel.

The variety of stent designs is determined, on the one hand, by the fact that the metal intravascular scaffolding must perform the vessel dilation and, on the other hand, must safely avoid penetration of the vessel wall or causing stenotic particles or thrombi to enter the blood flow. The stent should not injure the surrounding tissues that could take place during placement of the stent in the desired location of the pathological formation in the vessel, should not crumple upon the effect of blood pressure and the muscular influence, and should not deform and slide off the uninflated or not fully inflated dilatation balloon during delivery.

But the most important desired characteristic of a stent is that the stent should, as much as possible, have properties similar to the properties of the vessel itself. More particularly, the stent should not substantially correct the vessel hemodynamics, limit the vascular tissue pulsation, interfere with its blood flow, etc.

P. Ruygrok and P. Serruys, generalizing the results of the accumulated observations and the necessity of systematic increase in antithrombotic properties, recommend that the optimal stent design be provided with the following properties: flexibility, trackability, low profile, visibility, thromboresistance, biocompatability, reliable expandability (see "Calculation", Vol. 94, No. 5, Sep. 1, 1996). Presumably, the creation of a stent meeting the above-mentioned requirements, as well as its equipment by a temporary constructive element for local drug delivery, is an efficient means for the reducing a systematic anticoagulation therapy, bleeding and vascular complications after a significant traumatic influence to which the deforming scaffolding of the vessel belongs.

The above enumerated recommendations for stent design are generally recognized. However, these recommendations cannot alone be used for stent design since they are devoid of criterion evaluations. It is natural that the clinical practice requires the specification and quantification of some stent basic properties that are to a considerable extent suitable for their use by the creators of new designs.

A number of requirements, adopted from the clinical practice and, in particular, formulated by Dr. Martin E. Leon (Cardiology Research Foundation, New York) could be stated as follows:

1. There should be sufficient metal coverage by the stent of the vessel lesion parts. For the vessels with a diameter of 3 to 4 mm, the metal coverage should be about 15 to 25%, reaching 30% in SVG segments with a diameter of about 5 mm.

2. The stent must have areas of differing qualitative properties, along its longitudinal axis. In particular, along the edges the stent struts should be more rigid, while in the stent middle part the stent struts should be more flexible.

3. It is necessary to ensure the axis perpendicularity and sufficient rigidity of the stent end face surfaces.

4. Preferably a stent will behave like a closed stent, but have the flexibility of an open stent.

5. In the stent, after expansion, the relatively small distances between the struts, about 1 mm, should be preserved.

6. The stent should operationally preserve invariable the radial sizes. This is connected with the non-admission of stent metal relaxation after expansion (no recoil).

7. It is desirable to have the stent length of from about 8 to 40 mm. A stent length less than 8 mm makes it difficult to ensure its stable location in a vessel, and a stent length more than 40 mm makes it difficult to place it effectively due to complicated anatomical outlines of the vessel. For example, if long coverage by a stent of the vessel lesion is needed, it will be better to implant several stents of a shorter length in consecutive order.

8. It is undesirable to change a stent's axial sizes upon its final expansion in a vessel.

9. Upon the stent expansion in a vessel the operational pressure of the guiding catheter balloon should not exceed 8 atm.

10. The stents of the considered class should have the necessary diameters from 2.0 mm to 5 mm.

11. The overall stent design should be capable of creating specialized models, such as, for example, a V-shaped stent with a special protection of pair vessels carina area, etc.

It is supposed that in the near future the number of various stent designs will become unlimited, though the expediency of the problem solution requires the creation of no more than ten different modifications, sufficiently universal and efficient models according to the generalized operational characteristics.

A balloon expandable sheet stent, in which the constructive elements are preliminarily formed in a shape of a stencil on the thin sheet metallic blank surface, is known (see the patent request PCT/IL 98/00189 from Apr. 21, 1998), as shown in FIG. 1. A stencil comprises two relatively rigid bands (2, 3) whose branches form periodically repeating winding outlines (4) which, in the stent expandable shape, take the form of the semicircles, placed one after another oppositively in relation to the relatively rigid bands (2, 3) in an alternative sequence along the stent longitudinal axis.

Such a location of the stent semicircles (5,7) with a side view on the relatively rigid bands (6) location plane is schematically shown in FIG. 2. The prototype-stent has high functional properties and, in general, corresponds to the requirements demanded from such designs. The stent constructive elements, circular in the light, allow to register its diameter with precision. Besides, the semicircles arch-shape possesses a heightened stability that makes it possible to use thin blanks in a stent metal cover that can stand pressures, including extreme ones, from the side of the pulsating vessel, and at the same time the semicircles arch-shape has a good capacity of shape-retention after the removal of the guiding catheter balloon pressure (no recoil).

The relatively rigid bands (2, 3) reliably ensure the stent axial lengths. Also, such a stent design has high technological possibilities that are determined by the capacities of creating a volumetric device from the thin sheet metallic blank without applying the known connecting means (welding, soldering, lock connections, etc.).

However, the prototype-stent has some essential drawbacks. To create a stent tube form the neighboring semicircles are folded into opposite sides, thus making the clearance between the neighboring semicircles (5, 7), but folded into one side, an increased one. For a number of cases this fact limits the use of a stent in the clinical practice. Moreover, the semicircles alternation along the longitudinal axis, shown in FIG. 2, creates on the stent end faces some "steps", contrary to the notion that the stent axis end will be perpendicular.

This stent design, as well as the majority of the known clinical models, possesses the same monotonous properties along its entire extent. This does not always correspond in its extent to the anatomical properties of a vessel, especially to that with the pathological changes, requiring correction of the angioplasty. In addition there are some definite differences in the hemodynamics inside the stenting and those sections of the vessel that adjoin it. The consequences of such differences may turn out to be a reason for restenosis. It is obvious that when the stent end faces are designed, a special approach should be used.

Attention should be drawn to the fact that the perpendicularity of stent axis end faces is very important for all stents, without exception. That is why the whole complex of end face problems is one and the same for all the stents, irrespective of the variety of different designs.

In addition, the area of vessel metal coverage in the prototype-stent does not fully meet the requirements of clinical practice since it makes up less than 13% for the arteries with a diameter of about 3 to 4 mm.

OBJECTS OF THE INVENTION

It is an object of the invention to provide an improved stent design.

It is also an object of the invention to provide a balloon expandable stent comprised of alternating circles.

It is a further object of the invention to provide an improved stent design having a double-sheet or layer construction wherein the stent has unexpected radial strength.

These and other aspects of the invention will become more apparent from the discussion below.

SUMMARY OF THE INVENTION

A purpose of this invention is to create a stent with a common circular structure of constructive elements, not as a "alternating semicircles" system but in a shape of alternating circles. This arrangement realizes more efficiently the attainment of end face perpendicularity and the increase in the percentage of metal coverage of a vessel by the stent.

Another purpose of the invention is that the conditioned stent functional properties can change along its entire extent. For example, the local increased metal coverage of the vessel wall can be attained precisely in places where this is dictated by the intravascular diagnostics results, and the hemodynamics on the stent end faces sections can be improved with the help of the preconditioned change in these sections' geometry.

Both of the above purposes of the invention can be achieved with the use of the simple thin sheet metallic blanks, chiefly with consistent or uniform geometrical parameters along the entire extent of the said blanks. The double-sheet stent of the invention is formed from constructive elements, preliminary formed in a shape of two substantially similar stencils, on two sheet metallic blank surfaces. Each stencil comprises two relatively rigid bands, with branches forming periodically repeating winding outlines of a preconditioned width, located one after another and oppositely in relation to the relatively rigid bands in a consecutive alternation along the stent longitudinal axis, whereas the distance between the neighboring branches is greater than the said width of the said winding outlines. In the stent expanded shape, the winding outlines take up the form of semicircles.

In the double-sheet stent the constructive elements stencils are preliminarily superimposed one on another in such a way that they turn out to be shifted for the winding outline width along the stent longitudinal axis and form the alternating parts of the winding outlines whereas one pair of the winding outlines is executed by the simple superimposing of one stencil winding outline on a second stencil winding outline, while the neighboring pair of the winding outlines is executed by the superimposing of the second stencil winding outline on the first stencil winding outline, for which purpose the winding outlines of the second stencil are passed through the slots between the winding outlines of the first stencil. In the stent expanded shape the semicircles formed are located by turns, one semicircle belongs to the first stencil, while the neighboring semicircle belongs to the second stencil, and this sequence of the semicircles located along the stent longitudinal axis is preserved from the one side as well as from the opposite side of the doubled relatively rigid bands.

In the double-sheet stent the constructive elements first and second stencils are preliminarily superimposed one on another so as to shift for the width of the winding outlines along the stent longitudinal axis and to form the winding outlines' alternating parts, whereas each of the first stencil winding outlines is passed through the slots between the second stencil winding outlines against the stop of the first stencil winding outline branches into the branches of the second stencil winding outlines. In the stent expanded shape all formed semicircles of the first stencil are located on one side over the first stencil's relatively rigid band, and all formed semicircles of the first stencil are located oppositively on the other side over the relatively rigid band of the second stencil.

In the double-sheet stent the constructive elements first and second stencils, oriented definitely along the winding outlines, are spread one in relation to another for 180° after which the first stencil is superimposed on the second stencil, then the first stencil winding outlines are passed through the slots between the second stencil winding outlines against the stop of the winding outlines branches of the first stencil into the branches of the second stencil winding outlines, while in the stent expanded shape all formed semicircles of the second stencil are located on one side over the relatively rigid band of the first stencil, and all formed semicircles of the first stencil are located oppositively on the other side over the relatively rigid band of the second stencil.

In the double-sheet stent the distance between the semicircles along the stent longitudinal axis for the SVG segments with a diameter of about 5 mm is adjusted within the limits of the values' difference, the distance between the neighboring semicircles and the preconditioned winding outlines width, while for the arteries with a diameter of about 3 to 4 mm, that require a greater distance between the semicircles, the distance between the neighboring semicircles is increased.

In the double-sheet stent for the relatively large vessels the constructive elements of said first and second stencils, the outlines of the future stent semicircles are executed as rectilinear ones.

In the double-sheet stent one of the constructive elements stencils is executed in a shape of the fragments of another stencil, taken for a basic one, and the total length of the said fragments is less than the length of the said basic stencil, while the fragments are located in the preconditioned places along the stent longitudinal axis on the basic stencil.

In the double-sheet stent on the end faces of the basic stencil the constructive elements fragments are set up so that in the stent expanded shape the bordering with the end faces winding outlines of the basic stencil and those of the fragments each form a closed circle, whereas the perimeters of the bordering winding outlines, not less than two, are increased in relation to the other winding outlines perimeters that are executed equal.

Thus, as result of using two sheet metallic stencils, connected in the proposed manner without the use of any known connecting means (lock connections, etc.),it was possible to create a stent design consisting practically of alternating circles.

Therefore, in the stent area, falling at a unit of its length, there is a twice greater number of semicircles, comprising circles, i.e., twice as much of a metal area covering the wall of a vessel. Then, if in the prototype-stent the percentage of the said metal area totaled about 13%, in the proposed stent it makes up about 26%, that meets the requirements of the clinical practice. In this case, the stent circular structures automatically ensure the perpendicularity of its axis end faces that also meets the requirements of the clinical practice made to the stents since they improve hemodynamics and lower the risk of restenosis.

In the volume of the proposed stent design it is possible to increase locally the area of the vessel wall metal coverage with the help of the constructive elements fragments connected with the stent basic part. For example, if plaques in a vessel are remote one from another along its entire extent, then the said constructive elements fragments are set up in accordance with the location of plaques and in these places the vessel wall is protected safely enough. And in the intervals, where the plaques are absent, i. e. there where the fragments are not set up on the stent basic part, the area of the vessel wall metal coverage is twice as less and, consequently, the vessel wall section, washed by the blood, is twice greater, the fact that to a considerable extent contributes to increasing the viability of the artificial vessel in the indicated place.

In the proposed stent there are sections, where, irrespective of the place of pathological formation location in a vessel, the constructive changes are obligatory. Such places in the stent are the sections adjoining its end faces. Here is the boundary of hemodynamics change upon passing from the artificial part to the natural part of the vessel (or from the natural part to the artificial one). In the proposed stent design, by using the fragments connected with the stent basic part, the measures are taken to lessen the hemodynamics edge effect consequences on the indicated parts of the vessel (boundaries of blood flow change), as a result of which a peculiar infuser is formed at the inlet to an artificial vessel part, while at the outlet from the artificial vessel part a peculiar confusor for the blood flow. The lessening of the hemodynamics edge effects consequences decreases, by the indicated means, the risk of restenosis both on the artificial vessel sections and in the sections adjoining it. In this case, the stent end faces are perpendicular to its axis and preserve this property due to the heightened rigidity.

BRIEF DESCRIPTION OF THE DRAWINGS

This invention is herein described with the help of examples and references to the accompanying drawings, wherein:

FIG. 3 shows two similar stent constructive elements stencils I and II, prepared for unification in a double-sheet stent, according to the invention; and in FIG. 3a the stencils I and Ii are connected into one surface;

FIG. 4 shows schematically, in a lateral view, the beginning of the assembly of the double-sheet stent in which the distance between the planes of the relatively rigid bands is conditionally increased. The broken lines correspond to stencil II of the stent constructive elements;

DETAILED DESCRIPTION OF THE INVENTION

Figure 1:
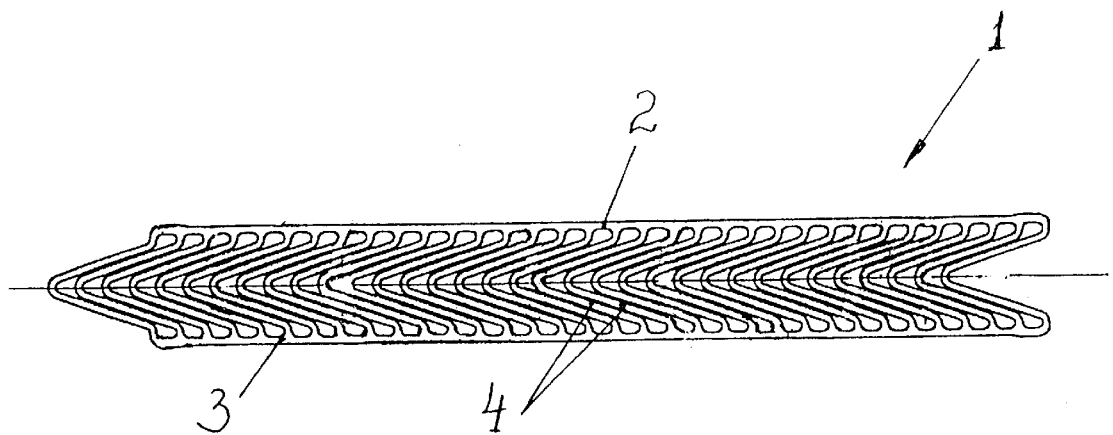
FIG. 1 shows the prototype-stent constructive elements' stencil, preliminarily formed on the thin sheet metallic blank surface.

The invention can perhaps be better appreciated by referring to the drawings. FIG. 3 shows two similar stent constructive elements stencils I and II, formed on the two thin sheet metallic blank surfaces. To prepare a double-sheet stent according to the invention, the stencil I constructive elements are superimposed on the stencil II constructive elements, matching the winding outlines (8, 9) with winding outlines (10, 11).

This is illustrated as an example of matching the winding outlines. The other winding outlines of stencils I and II are located in the same manner (the stencils I and II matching operation itself is not shown in FIG. 3). Then, stencil I is shifted to the right along the longitudinal axis of stencil II for the winding outline width by FIG. 3.

In FIG. 3a a double sheet stencil is formed from two similar stent constructive elements stencils I and II. In this case, the stencils I and II are connected into one surface along common longitudinal axis of the thin sheet blank by a relatively rigid band in such a way that the stencil I winding outlines (8, 9) are the continuation of the stencil II winding outlines (10, 11) with a shift of the winding outlines (10, 11) in relation to the winding outlines (8, 9) along the relatively rigid band for a width of a winding outline.

The double sheet stencil in FIG. 3a can be bent along the fold line of the thin sheet blank common longitudinal axis, the stencil II winding outlines (10, 11) are passed through the stencil I winding outlines (8, 9) slots each time over one winding outline. Alternatively, the double sheet stencil can be folded, joining relatively rigid bands and forming an upsplit joint, or the double sheet stencil can be formed directly on a tubular blank with the wall width equal to that of the thin sheet blank.

For all three variations evolving from FIG. 3a, radial expansion of double sheet stencil forms the single stent alternating circles.

FIG. 4 schematically represents the shifting to the right of stencil I in relation to stencil II. The stencil I winding outlines (12, 13) corresponding to positions (8, 9) of FIG. 3, and the stencil II winding outlines (14, 15) corresponding to positions (10, 11) of FIG. 3 interact, thus uniting the stencil I and stencil II constructive elements into the double-sheet stent configuration. The winding outlines (12) and (14) are simply superimposed one on another (with the above-mentioned shifting), while the winding outline (15), belonging to stencil II, is passed through the slot between stencil I winding outlines. As a result, in the first described pair the stencil I winding outline, i.e., (12), is superimposed on the stencil II winding outline, i.e., (14), and in the second described pair the stencil n winding outline, i.e., (15), is superimposed on the stencil I winding outline, i.e., (13). All the other winding outlines interact in the same way. If to look from above along the arrow A, then the visible winding outlines of stencils 1 and II follow one another, alternate (12, 15, etc.). At the same time, if to let the gauge pass through the winding outlines lying above (12, 15, etc.) and start folding them into one side, upwards, while all the other winding outlines fold downwards, thus increasing simultaneously the diameter of the gauges, then a stent from the constructive elements stencils I and II is formed.

Figure 5:
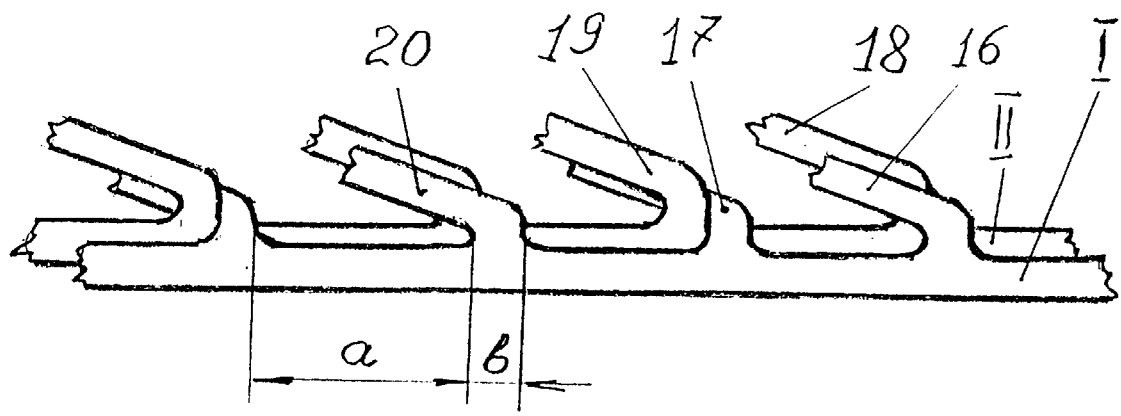
FIG. 5 represents a fragment of an assembly of the stent constructive elements stencils I and II, according to the invention. This is a view in the direction of arrow A in FIG. 4, where sections B and C in FIG. 3, superimposed one on another by the preconditioned way. Here, "a" is the distance between the winding outlines branches and "b" is the width of the winding outline.

FIG. 5 shows fragments of winding outlines of stencils I and II outlines in a situation, corresponding to that described by FIG. 4. Here, only the winding outlines 'initial parts, with the connection on the two relatively rigid bands 2a, are depicted, the fact that corresponds to the fragment B of stencil I and the fragment C of stencil II by FIG. 3. Elements (16, 17) of FIG. 5, belonging to the stencil I winding outlines, correspond to elements (12, 13) of FIG. 4, belonging to the same stencil I winding outlines. Elements (18, 19) of FIG. 5, belonging to the stencil II winding outlines, correspond to elements (14, 15) of FIG. 4, belonging to the same stencil II winding outlines.

In FIG. 5 the situation described by FIG. 4, is better illustrated. Here is seen the alternation of stencils I and II winding outlines, i.e., elements (16, 19, etc.).

In FIG. 5 the indicated winding outlines are turned to the observer of this Figure, while the winding outlines (18, 17) are located under them. The winding outline (16) is simply superimposed on the winding outline (18), and the winding outline (17), passing through the slot between stencil II winding outlines, turned out to be under the winding outline (19). Then, if the winding outlines (16, 19) are to be folded towards the observer of FIG. 5, and the winding outlines (18, 17) towards the opposite side, the indicated winding outlines will form practically two circles after the calibration. The winding outlines (16, 18) form one circle, while the winding outlines outlines (17, 19) form another one. In this case, the semicircles, obtained from the winding outlines (16, 19), are directed towards one side, i.e., to that of the observer of FIG. 5, while the semicircles, from the winding outlines (18, 17), are directed towards the opposite side, i.e., from the observer of FIG. 5.

Figure 2:
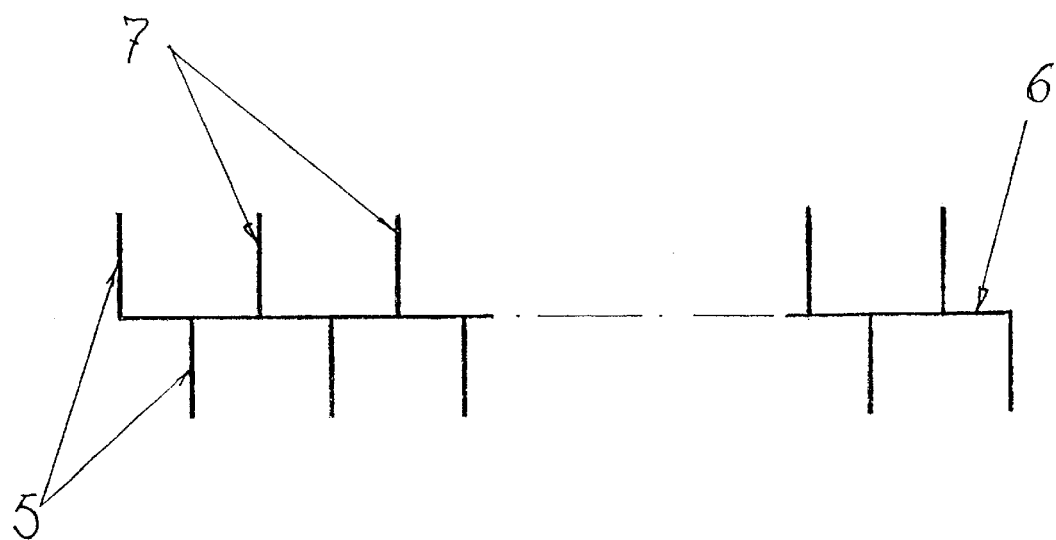
FIG. 2 shows schematically the consecutive alternation of the semicircles along the prototype-stent of FIG. 1 longitudinal axis upon the side view on the location plane of the relatively rigid bands.
Figure 6:
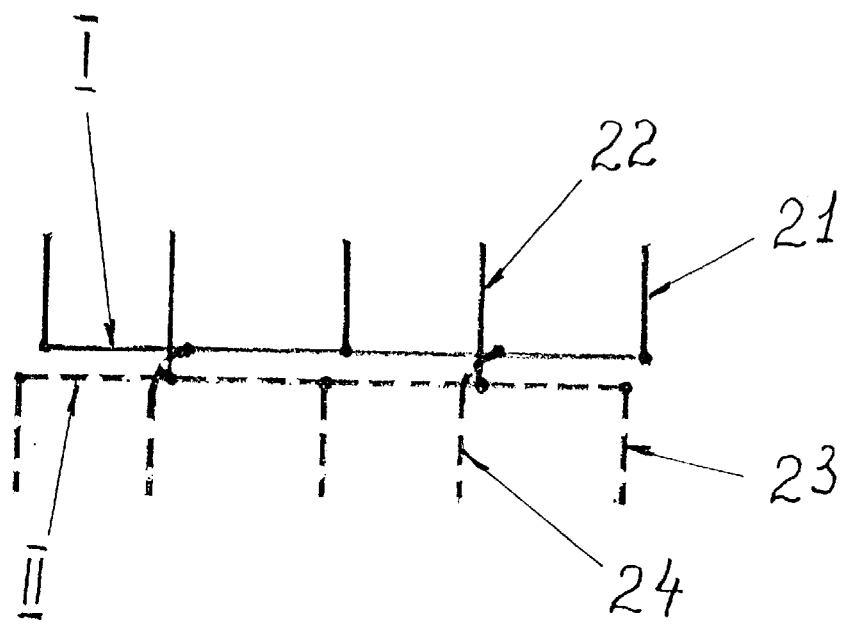
FIG. 6 shows schematically a lateral view of the location of the stent relatively rigid band semicircles, according to the invention. Variant by FIG. 5. The broken lines correspond to the constructive elements stencil II.

FIG. 6 shows schematically the location of the stent semicircles after expansion upon a side view on the relatively rigid bands location plane. By positions (21, 22) are depicted the upper neighboring semicircles of stencils I and II that correspond to positions (16, 19) of the winding outlines by FIG. 5. By positions (23, 24) are depicted the lower neighboring semicircles of stencils I and II that correspond to positions (18, 17) of the winding outlines by FIG. 5. FIG. 6 shows conditionally that semicircle (24) passed through semicircle (22). This was done in accordance with the previously described explanation by FIG. 5 of the fact that the stencil I winding outline (17) passes into the slot between the stencil II winding outlines, locating under the stencil II winding outline (19) and forming, upon the stent expansion, the lower semicircle (24 of FIG. 6). The depicted operation is repeated along the stent entire axial length. FIG. 6 shows a variant of the double-sheet stent when the semicircles actually form the closed circles. It is seen, as a result, that the stent end faces surfaces do not have steps and turn out to be perpendicular to the stent longitudinal axis, while vessel wall metal coverage increases twice as much in comparison with the prototype-stent (see FIG. 2).

Figure 7:
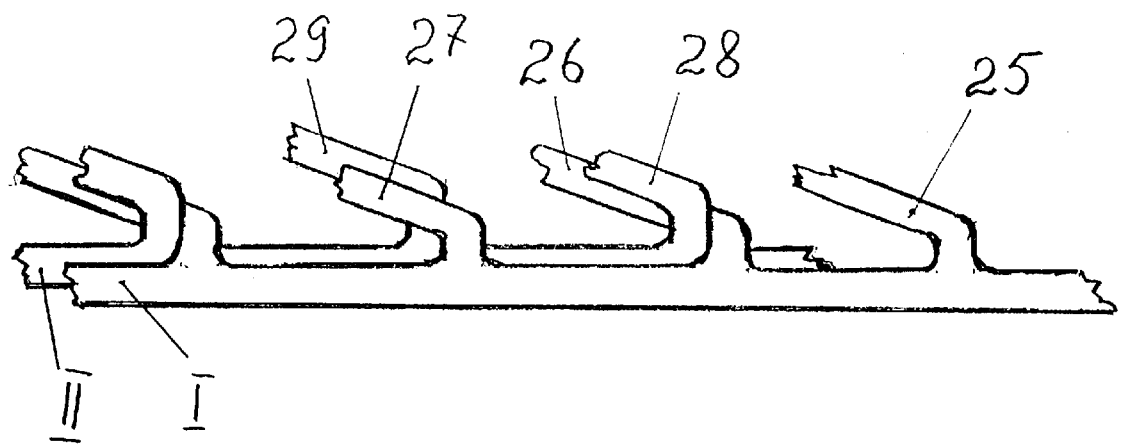
FIG. 7 shows a fragment of the stent constructive elements stencil I and II assembly, according to the invention. This is a view along the arrow A in FIG. 4, sections where B and C in FIG. 3, superimposed one on another by a preconditioned way.

FIG. 7 shows the same as FIG. 5, only with the different relative location of the winding outlines of stencils I and II. Elements (25, 26, 27) of FIG. 7, belonging to the stencil I winding outlines, correspond to elements (16, 17, 20) of FIG. 5, belonging to the same stencil I winding outlines. Elements (28, 29) of FIG. 7, belonging to the stencil II winding outlines, correspond to elements (18, 19) of FIG. 5, belonging to the same stencil II winding outlines. The different location of stencils in FIG. 7 is determined by the shifting of stencil II in relation to stencil I of FIG. 5 to the left for a value of (a–b), where "a" is the distance between the winding outline branches and "b" is the width of a winding outline. The sizes "a" and "b" are shown in FIG. 5 since there it is easier to represent the stencils I and II shifting, leading to the location of the constructive elements, illustrated in FIG. 7. In this case, the uniting of stencils I and II constructive elements, described in connection with FIG. 5, leads to the forming by winding outlines (26, 28), corresponding to elements (17, 18) of FIG. 5 of two lower semicircles upon the stent expansion. The winding outlines (27, 29), corresponding to elements (20, 19) of FIG. 5, form two upper semicircles upon the stent expansion. As a result, the stent would consist of as though alternating double semicircles.

Figure 8:
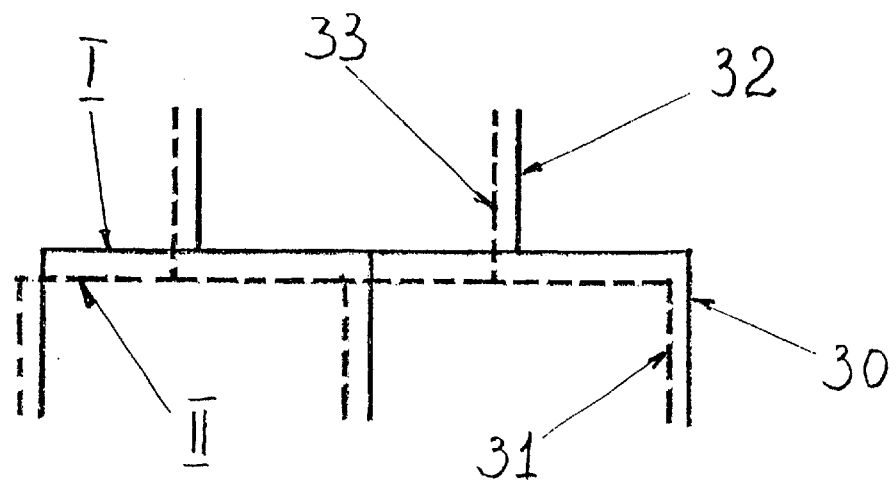
FIG. 8 shows schematically a lateral view of the location of the stent relatively rigid band semicircles, according to the invention. Variant by FIG. 7. The broken lines correspond to the stent constructive elements of stencil II.

FIG. 8 shows schematically the location of the stent semicircles upon a side view on relatively rigid bands location plane. By elements (30, 31) the lower neighboring semicircles ate designated, representing as though one lower double semicircle of the stent. Elements (30, 31) of the semicircles correspond to elements (26, 28) of the winding outlines of FIG. 7. By elements (32, 33) are designated the upper neighboring semicircles, representing as though one upper stent double semicircles. Elements (32, 33) of the semicircles correspond to positions (27, 29) of the winding outlines of FIG. 7.

From FIG. 8 it follows that the stent consists of double semicircles, i.e., the closing of the semicircles into closed circles as in the prototype-stent; however, the quantity of metal and, consequently, the vessel wall metal coverage is twice as much. It should be noted that to achieve such an effect in the prototype-stent by a technologically simple increase in the winding outline width is rather difficult. The transition from the stent configuration of FIG. 6 to the stent configuration of FIG. 8 is determined by the necessity to obtain, in some cases, the increased clearances between the semicircles (e.g., double ones). If necessary the clearance between the semicircles for the stents both of FIG. 6 and of FIG. 8 could also be conditionally widened at the expense of increasing the distance "a" between the branches (see FIG. 5). In this case, the width of slots between the stencils winding outlines increases correspondingly.

Figure 9:
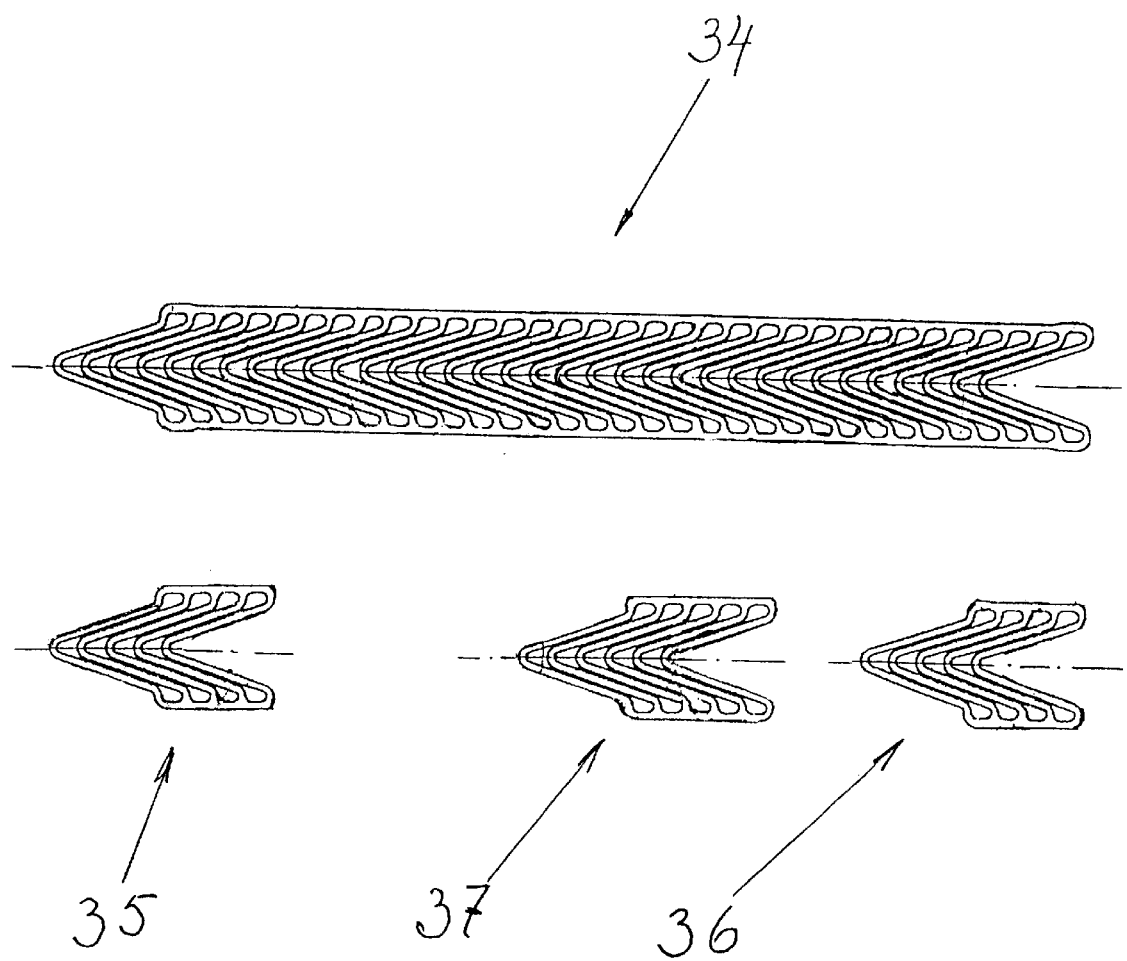
FIG. 9 shows the basic stencil and fragments of the stent constructive elements, according to the invention, prepared for unification in the double-sheet stent.

FIG. 9 shows the basic stencil (34) and fragments (35, 36, 37) of the stent constructive elements, prepared for unification in the double-sheet stent. Here, apart from the end faces, practically obligatory fragments (35, 36), the number and the axial sizes of the intermediary fragments (37) can be different depending on the clinical practice requirements. This emphasizes once more the individuality of the double-sheet stent design, though the stent is formed from the relatively simple (monotonous) components. Irrespective of the quantity and peculiarities of uniting the intermediary fragments (37) with the constructive elements basic stencil (34), the edge fragments (35, 36) must always be taken into account for strengthening the stent end faces and ensuring the end faces perpendicular to its axis. Therefore, the fragments (35, 36) are united with the constructive elements basic stencil (34) according to the schemes, corresponding to FIGS. 5, 6. The number of winding outlines in each of the fragments (35, 36) should not be less than two, while, practically, given the sufficient stent axial length, the number of the winding outlines in each of the fragments (35, 36) could be increased to seven.

In view of the importance of calculating the hemodynamic peculiarities in the stent end faces area, it is desirable to form something like a "bell-mouthed" effect at the inlet and outlet of the blood flow. For this purpose on fragments (35, 36), as well as along the basic stencil constructive element sections, corresponding to the length of these fragments, the stent circle diameters are increased gradually up to the very end face. It is obvious, that the most reasonable is the maximum increase of the diameter, i.e., at the very end face for 2 to 4 widths of the circle wall.

As is seen, the very insignificant increase in the diameter at the stent end faces is regulated. However, in this case the end faces, widening for the indicated value by the free end part of the guiding catheter balloon, install the end faces circles walls flash with the wall of a partially crashed through vessel. This ensures the creation of the peculiar infusor and confusor respectively at the stent inlet and outlet which improve the hemodynamics in the transitional regions of the "vessel-stent" system and in this way decrease the risk of restenosis. The recommended increase in the semicircles diameters at stent end faces is achieved by the increase in the corresponding winding outlines perimeters.

Figure 10:
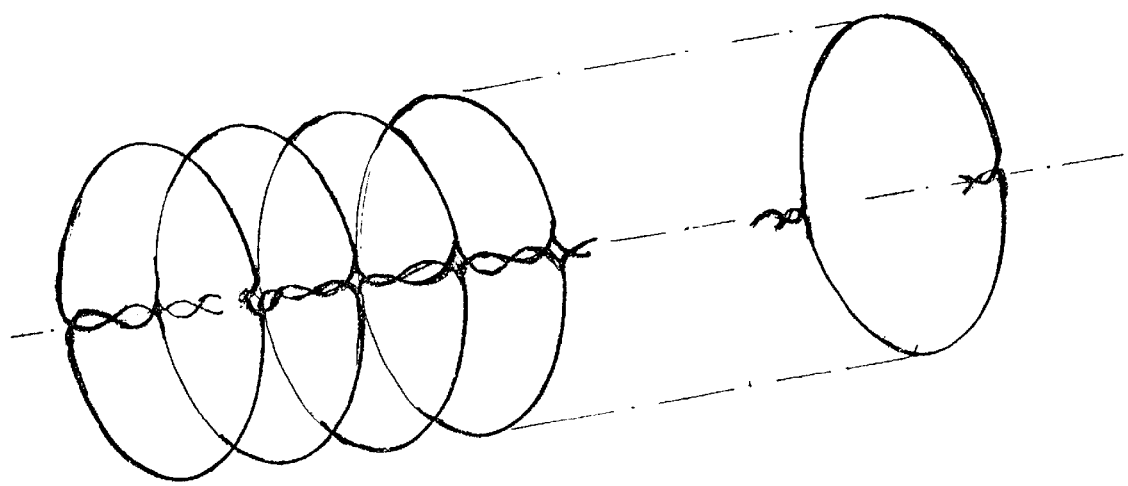
FIG. 10 shows schematically a fragment of the double-sheet stent after expansion, according to the invention.

FIG. 10 shows a fragment of the stent exterior, according to the invention, widened in accordance with FIG. 6, where the semicircles actually form the closed circles.

Figure 11:
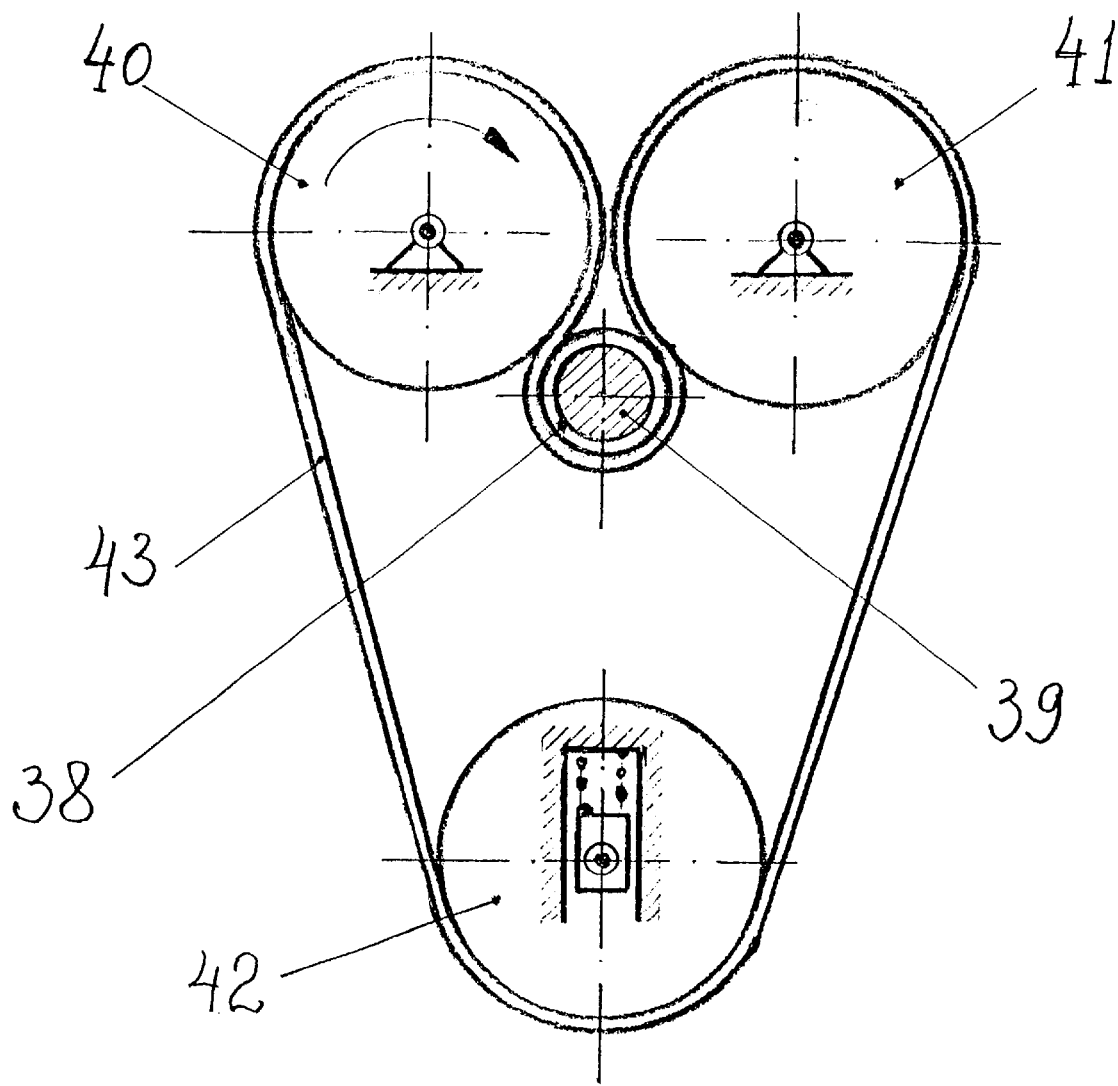
FIG. 11 shows schematically the stent overall diameter reduction on the mandrel to the sizes necessary for the location on the guiding catheter uninflated balloon.

FIG. 11 shows schematically the stent overall diameter reduction on the mandrel to the sizes necessary for the location on the guiding catheter uninflated balloon and implantation in a vessel. The reduction is done with the help of rollers (40, 41) and a tension reel (42) with an elastic ribbon (43), the width of which corresponds to the regulated stent length. The rigidity of the elastic ribbon (43) should be less than the rigidity of the stent material. For example, the nylon ribbon could be used. The elastic ribbon (43) densely envelops the stent (38) on the mandrel (39), pressing it partially to the rollers (40, 41). The tension reel (42) effort should be sufficient for stent volume reduction, but not too great, as not to damage the ribbon (43) and the stent (38) at the place of their compression to the rollers (40, 41). Upon the rollers (40, 41) rotation the secure stent volume reduction up to the minimum sizes is performed, the sizes that depend on the rigid metallic mandrel (39) diameter.

Thus, as is described herein, the stent design of the invention is formed by a circular structure, i.e., the stent consists of a row of closed circles connected with each other. The presence of the closed circles on the stent end faces make it possible to provide end faces that are perpendicular to the stent's longitudinal axis. It is shown that the metal coverage of the vessel wall, as compared with the prototype-stent, increases two times more, i.e., actually grows from 13 to 26%. In this case, a lumen between the stent circles could be established beforehand in accordance with the clinical practice requirements. Due to the use of constructive elements fragments, connected with the basic stencil, the stent functional possibilities are widened. In the proposed design the local metal coverage of the vessel wall is possible only in the places preliminary determined by the intravascular diagnostics. As a consequence of this, the relatively healthy vessel wall sections are more intensively washed by the blood, thus contributing to the increase in their viability. The fragments, set up on the stent end faces, increase their rigidity, while a special proposal on the stent circles geometry ensures the obtaining of "bell-mouthed" effect at the stent edge sections, thus contributing to the hemodynamics improvement and, as a consequence, decreasing the risk of restenosis.

The technology of the proposed stent design is preserved at the level of the prototype-stent with a certain increase in the assembly operations cycle.

A possibility of the confident obtaining of the stent minimal diameter, necessary for its normal guidance and implantation in the vessel, is shown with a help of a relatively simple device.

The preceding specific embodiments are illustrative of the practice of the invention. It is to be understood, however, that other expedients known to those skilled in the art or disclosed herein, may be employed without departing from the spirit of the invention or the scope of the appended claims.

What is claimed is:

1. A double-sheet stent for insertion in a lumen of a vessel of living being, comprising:

constructive elements, preliminary formed in a shape of the two mainly similar stencils I and II on the surfaces of the two thin sheet metallic blanks, each of which is represented by the two relatively rigid bands, the branches of which form a periodically repeating winding outlines of a preconditioned width and which in a stent expanded shape take the form of semicircles, located one after the other oppositively in relation to the said relatively rigid bands in a consecutive alternation along the stent longitudinal axis, whereas the distance between the neighboring branches is greater than the winding outlines width;

the constructive elements stencils I and II are preliminary superimposed one on another so as to be shifted for a winding outline width along the stent longitudinal axis and form the alternating winding outlines pairs, whereas one pair of the said winding outlines is executed by the simple superimposing of stencil I winding outline on stencil II winding outline, while the neighboring pair of the said winding outlines is executed by the superimposing of stencil II winding outline on the winding outline of stencil I, for which purpose the winding outlines of stencil II are passed through the slots between winding outlines of stencil I, and in the stent expanded shape the formed semicircles are located by turns, one semicircle belongs to stencil I, while the neighboring semicircle belongs to stencil II, and this sequence of the said semicircles location along the stent longitudinal axis is preserved both from the one side, as well as from the opposite side of the said doubled relatively rigid bands;

the constructive elements stencils I and II are preliminary superimposed one on another so as to shift for a said width of the winding outlines along the stent longitudinal axis and to form the winding outlines alternating parts, whereas each of the winding outlines of stencil I is passed through the slots between the winding outlines of stencil II against the stop of the said winding outlines branches of stencil I into the branches of the winding outlines of stencil II, while in the stent expanded shape all the formed semicircles of stencil II are located on one side over the the relatively rigid band of stencil I, and all formed semicircles of stencil I are located oppositively on the other side over the relatively rigid band of stencil II;

the constructive elements stencil I and II, definitely oriented along winding outlines and are spread one in relation to another for 180°, then stencil I is superimposed on stencil II, then pass the said stencil I winding outlines into the slots between the stencil II winding outlines against the stop of the winding outlines branches of stencil I into the branches of the winding outlines of stencil II, while in the stent expanded shape all formed semicircles of stencil II are located on one side over the relatively rigid band of stencil I, and all formed semicircles of stencil I are located appositively on the other side over the relatively rigid band of stencil II; for the SVG segments with a diameter of about 5 mm the distance between the said semicircles along the stent longitudinal axis is adjusted within the limits of the said values difference, the distance between the neighboring semicircles and preconditioned winding outlines width, while for the arteries with a diameter of about 3 to 4 mm, that require a greater distance between the semicircles, the distance between the neighboring semicircles is increased;

for the relatively large vessels in the said stencil I and II the constructive elements, the winding outlines of the stent future semicircles, are executed as rectilinear ones.

2. The double-sheet stent of claim 1, in which one of the constructive elements stencils is executed in a shape of the fragments of another stencil, taken for a basic one, the fragments' total length is less than that of the said basic stencil, and the fragments are located in the preconditioned places on the basic stencil along its longitudinal axis.

3. The double-sheet stent of claim 2, in which the constructive elements fragments are set up on the basic stencil end faces in such a way that in the stent expanded shape the basic stencil winding outlines, the ones bordering with the end faces, each form a closed circle, whereas the perimeters of the bordering winding outlines, not less than two, are increased in relation to the other winding outlines perimeters that are executed equal.

4. The double-sheet stent of claim 1, in which the volumetric structures are formed from the stencils I and II in a shape of alternating semicircles with a possibility of their axial alignment, where one of the volumetric structures is introduced into another volumetric structure, while upon the radial expansion of the united semicircles the single stent alternating circles are formed.

5. The double-sheet stent of claim 1, in which the stencils I and II are connected into one surface along the common longitudinal axis of the thin sheet blank by a relatively rigid band in such a way that the stencil I winding outlines are the continuation of the stencil II winding outlines with a shift of the winding outlines one in relation to the other along the relatively rigid band for a width of a winding outline, whereas the winding outlines of the thin sheet blank edges are connected along the said common longitudinal axis by two relatively rigid bands, thus forming a double-sheet stencil, the double-sheet stencil is bended along the fold line of the thin sheet blank common longitudinal axis, the stencil II winding outlines are passed through the stencil I winding outlines slots each time over one winding outline, while upon the radial expansion of the united double-sheet stencil the single stent alternating circles are formed.

6. The double-sheet stent of claim 1 or 2, wherein the double-sheet stencil of which the cross-section of the relatively rigid bands is executed of another value, in particular, of a lesser one, in comparison with the cross-section of the said winding outlines.

7. The double-sheet stent of claim 1 or 2, wherein the stencils I and II contain a great number of V-shaped winding outlines the angles of which are turned to one side.

8. The double-sheet stent of claim 1 or 2, wherein the stencils I and II contain a great number of Z-shaped winding outlines with both angles turned to the opposite sides.

9. The double-sheet stent of claim 1 or 2, wherein the stencils I and II contain a great number of the said winding outlines and make up a form that includes more than two angles directed by turns into the opposite sides.

10. The double-sheet stent of claim 1 or 3, wherein the stencils I and II are connected into one surface along common longitudinal axis of the thin sheet blank symmetry by one relatively rigid band in such a way that the stencil I winding outlines are the continuation of the stencil II winding outlines, but the winding outlines of the thin sheet blank edges are connected along the longitudinal axis by the two relatively rigid bands, thus forming a double-sheet stencil, the double-sheet stencil is folded, joining the said last relatively rigid bands and forming an unsplit joint, whereas in a stent expanded shape all the stencil I formed semicircles are located on one side from the location surface of the relatively rigid bands and all the stencil II formed semicircles are located oppositively on the other side from the location surface of the relatively rigid bands.

11. The double-sheet stent of claim 1, wherein the winding outlines of the stencils I and II are connected directly between themselves in the double-sheet stencil.

12. The double-sheet stent of claim 1, wherein the longitudinal axes of the two doubled winding outlines form the "V" pattern of the future V-shaped stent corresponding two longitudinal axes.

13. The double-sheet stent of claim 1, wherein the longitudinal axes of the three doubled winding outlines form the "Y" pattern of the future Y-shaped stent corresponding three longitudinal axes.

14. The double-sheet stent of claim 1, wherein the double-sheet stencil is executed directly on the tubular blank with the wall width equal to that of the said thin sheet blank.

15. The double-sheet stent of claim 1 or 2, wherein the winding outline, and in particular, for the stents with the diameter expansion of 3.0 mm more, is executed symmetrically in relation to a line connecting the fastening places of the winding outlines, by the shortest possible way, with the relatively rigid bands, whereas upon the expansion of the future stent this line will be a symmetry line of the forming semicircle.

16. The double-sheet stent of claim 1 or 2, wherein the stent blank width is calculated in such a way that upon the stent expansion by the balloon pressure of 6 atm. the nominal diameter of the expanded stent is obtained, whereas every winding outline, forming a semicircle, is executed with a possibility of preserving the outline curvature, determined by the size of the angle between the outline constructive elements not less than 135°.

17. The double-sheet stent of claim 16, wherein the possibility of increasing the nominal diameter of the already expanded stent in the limits up to 14% is ensured, for which the pressure in the balloon is raised from 6 atm. up to 14 atm.

18. A double-sheet stent for insertion into a lumen of a vessel of a living being, comprising:
  a first constructive member comprising two substantially parallel first longitudinal members having a double sheet multitude of first connecting members attached to and positioned between said first longitudinal members; and
  a second constructive members having two second substantially parallel longitudinal members having a multitude of second connecting members attached to and positioned between said second longitudinal members connected therebetween,
  wherein the first constructive members are superimposed one upon another and the first and second connecting members are arranged out of the plane of the first and second constructive members to form a tubular structure.

19. The double-sheet stent of claim 18, wherein each constructive member comprises a thin metallic blank.

20. The double-sheet stent of claim 18, wherein the longitudinal members are relatively rigid.

21. The double-sheet stent of claim 18, wherein the connecting members form periodically repeating winding outlines of a predetermined width.

22. The double-sheet stent of claim 18, wherein in the expanded shape the connecting members take the form of semicircles.

23. The double-sheet stent of claim 18, wherein the first connecting members and the second connecting members are positioned one after the other oppositely in relation to the longitudinal members in consecutive alternation along the longitudinal axis of the stent.

24. The double-sheet stent of claim 18, wherein the distance between the first and second connecting members, respectively, is greater than the width of each connecting member.

25. The double-sheet stent of claim 18, wherein the connecting members form alternating winding outline pairs.

26. The double-sheet stent of claim 18, wherein the first and second constructive elements are superimposed upon each other to the extent they are shifted a distance corresponding to the width of the connecting member.

27. The double-sheet stent of claim 18, wherein the connecting members of the first constructive member are passed through slots between connecting members of the second constructive member.

28. The double-sheet stent of claim 27, wherein the connecting members form alternating semicircles.

29. The double-sheet stent of claim 28, wherein each tubular half of the stent comprises semicircular members formed alternatingly from first and second connecting members.

30. The double-sheet stent of claim 28, wherein one tubular half of the stent comprises semicircles formed from first connecting members and the other half comprises semicircles formed from second connecting members.

31. The double-sheet stent of claim 18, wherein the constructive elements are definitely oriented arid are spread in relation to another for 180°.

32. The double-sheet stent of claim 31, wherein in the stent expanded shape all formed semicircles of the second constructive element are located on one side over a first longitudinal member.

33. The double-sheet stent of claim 18, in which the second constructive element comprises two or more fragmentary elements, each of said fragmentary elements comprising two substantially parallel longitudinal elements and connecting members attached to and positioned between said longitudinal members, wherein the total longitudinal length of the fragmentary elements is less than the longitudinal length of the first constructive element.

34. The double-sheet stent of claim 33, wherein the fragmentary elements are located in predetermined places on the first constructive element along its longitudinal axis.

35. The double-sheet stent of claim 33, wherein the fragmentary elements are arranged on the first constructive element so that in the stent expanded shape the connecting members bordering end faces of the stent each form a closed circle.

36. The double-sheet stent of claim 35, wherein the perimeters of the bordering connecting members, not less than two, are increased in relation to the other connecting members perimeters that are executed equal.

37. The double-sheet stent of claim 18, wherein volumetric structures are formed from first and second constructive elements in a shape of alternating semicircles with a possibility of axial alignment, where one of the volumetric structures is introduced into another volumetric structure, while upon the radial expansion of the united semicircles the single stent alternating circles are formed.

38. A method of preparing the double-sheet stent of claim 18, wherein the first and second constructive elements are connected into one surface along the common longitudinal axis by longitudinal members in such a way that the first connecting members are the continuation of the second connecting members with a shift of the connecting members one in relation to the other along the longitudinal axis for a width of a connecting member, whereas the respective connecting members are connected along the common longitudinal axis by two longitudinal members, thus forming a double-sheet stencil, the double-sheet stencil is bended along the fold line of the common longitudinal axis, the second connecting members are passed through the slots of the first connecting members each time over one connecting member, while upon the radial expansion of the united double-sheet stencil the single stent alternating circles are formed.

39. The double-sheet stent of claim 18 or 33, wherein the distance between the longitudinal members of the first constructive element differs from the distance between the longitudinal members of the second constructive element.

40. The double-sheet stent of claim 18 or 33, wherein the connecting members comprise a great number of V-shaped members, the angles of which are turned to one side.

41. The double-sheet stent of claim 18 or 33, wherein the connecting members comprise a great number of Z-shaped members with both angles turned to opposite sides.

42. The double-sheet stent of claim 40, wherein the connecting members make up a form that includes more than two angles directed by turns into opposite sides.

43. The double-sheet stent of claim 18 or 34, wherein the first and second constructive elements are connected into one surface along a common longitudinal axis of the thin sheet blank symmetry by one longitudinal member in such a way that the first connecting members are the continuation of the second connecting members, the connecting members are connected along the longitudinal axis by the longitudinal members, thus forming a double-sheet stencil, the double-sheet stencil is folded, joining the last longitudinal elements and forming an unsplit joint, whereas in a stent expanded shape all the first constructive element formed semicircles are located on one side from the location surface of the longitudinal elements and all the second constructive elements formed semicircles are located oppositively on the other side from the location surface of the longitudinal members.

44. The double-sheet stent of claim 18 or 33, wherein the connecting members are connected directly between themselves in the double-sheet stencil.

45. The double-sheet stent of claim 18, wherein the longitudinal axes of the two doubled connecting members form the "V" pattern of a V-shaped stent having two longitudinal axes.

46. The double-sheet stent of claim 18, wherein the longitudinal axes of the three doubled connecting members outlines form the "Y" pattern of a Y-shaped stent having three longitudinal axes.

47. The double-sheet stent of claim 18, wherein the double-sheet stencil is executed directly on a tubular blank with the wall width equal to that of the said thin sheet blank.

48. The double-sheet stent of claim 41 wherein the connecting members make-up a form that includes more than two angles directed by turns into opposite sides.

* * * * *